United States Patent [19]

Ryder et al.

[11] Patent Number: 5,118,381
[45] Date of Patent: Jun. 2, 1992

[54] TAPE DISPENSER AND METHOD

[75] Inventors: Francis E. Ryder, Arab; Joseph V. Ranalletta, Guntersville, both of Ala.

[73] Assignee: Ryder International Corporation, Arab, Ala.

[21] Appl. No.: 572,682

[22] Filed: Aug. 24, 1990

[51] Int. Cl.$^5$ .............................................. B32B 31/08
[52] U.S. Cl. .................................. 156/552; 156/289; 156/302; 156/538; 156/577
[58] Field of Search .............. 156/289, 302, 552, 577, 156/538

[56] References Cited

U.S. PATENT DOCUMENTS

| | | | |
|---|---|---|---|
| 4,574,030 | 3/1986 | Pilcher | 156/577 |
| 4,588,469 | 5/1986 | Hunter | 156/577 |
| 4,704,185 | 11/1987 | Fischer | 156/577 |
| 4,851,074 | 7/1989 | Uchida | 156/577 |
| 4,906,322 | 3/1990 | Hollier | 156/577 |

Primary Examiner—Robert A. Dawson
Assistant Examiner—David Reifsnyder
Attorney, Agent, or Firm—Trexler, Bushnell, Giangiorgi & Blackstone, Ltd.

[57] ABSTRACT

A tape dispenser apparatus for tape having an adhesive surface includes a first supply compartment for holding a continuous length of the tape and a second compartment for holding a plurality of individual tabs or cover members which can be successively removed from the second compartment and applied to portions of the adhesive tape surface to provide multiple, covered adhesive surface portions of the tape. The dispenser has guide structure for guiding displacement of the tape to the second compartment for the removal and adherence of the tabs or cover members. Two of the cover members can be applied to the adhesive surface in spaced sequence to form an expanse of the exposed adhesive surface between the covered portions so that the medial adhesive surface of the tape can be applied for example to a patient's eyelids or surgical dressings by manipulating the covered tape portions which thereby insulate the fingers of the manipulator from the adhesive tape surface, after which the cover members can be optionally removed.

38 Claims, 1 Drawing Sheet

TAPE DISPENSER AND METHOD

BACKGROUND OF THE INVENTION

This invention relates to dispensing apparatus for adhesive tape, and more particularly relates to improved convenience in dispensing and handling surgical tape.

During surgical procedures requiring application of typical surgical tape, the personnel conducting and assisting in the surgery wear conventional rubber surgical gloves which often adhere to the adhesive surface of the surgical tape resulting in awkward sticking and tearing of the gloves during the manipulated application of the tape. For example, an anesthesiologist may elect to tape the eyelids of a patient during the surgical procedure. The above discussed disadvantage is eliminated by the tape dispensing method and apparatus in accordance with the present invention.

SUMMARY OF THE INVENTION

In accordance with the present invention, a tape dispenser apparatus for tape having an adhesive surface includes a first supply compartment for holding a continuous length of the tape and a second compartment for holding a plurality of individual tabs or cover members which can be successively removed from the second compartment and applied to portions of the adhesive tape surface to provide multiple, covered adhesive surface portions of the tape. The dispenser has guide structure for guiding displacement of the tape to the second compartment for the removal and adherence of the tab or cover members. Two of the cover members can be applied to the adhesive surface in spaced sequence to form an expanse of the exposed adhesive surface between the covered portions so that the medial adhesive surface of the tape can be applied, for example to cover the eyelids of a surgical patient while under anesthetic or to hold in place surgical dressings, by manipulating the covered tape portions which thereby insulate the fingers of the manipulator from the adhesive tape surface, after which the cover members can be optionally removed.

In a preferred embodiment, the housing of the tape supply compartment has a guide aperture which is spaced relative to the second compartment holding cover members so that the displaced tape is guided along a path extending above the second compartment. The second compartment has a removal aperture through which the individual cover members pass upwardly into contact with the adhesive lower surface of the tape which is manually downwardly deflected or depressed to engage and pick up the cover members at the removal aperture. The cover members are preferably paper tabs which are vertically stacked within the second compartment and are seated upon biasing means in the form of a compressible sponge rubber element or a spring plate type element which upwardly biases the stack to successively feed the uppermost tab in the stack to the removal aperture at which the tape portion is deflected or depressed into the adhering contact with the tab and removed with the continued tape displacement.

DESCRIPTION OF THE ILLUSTRATED EMBODIMENT

Figure 1:
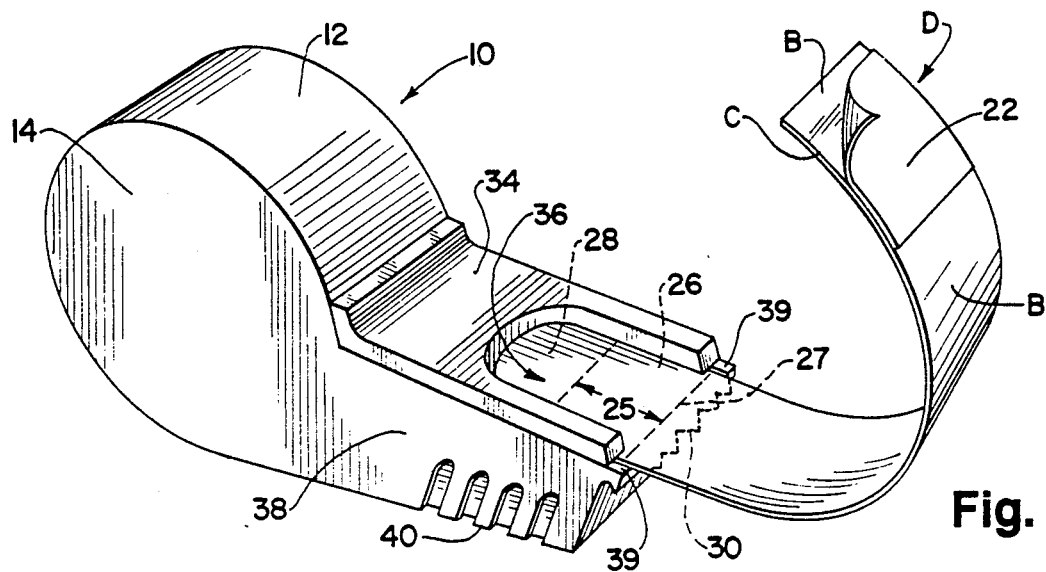
FIG. 1 is a perspective view of one embodiment of a tape dispenser in accordance with the invention.
Figure 2:
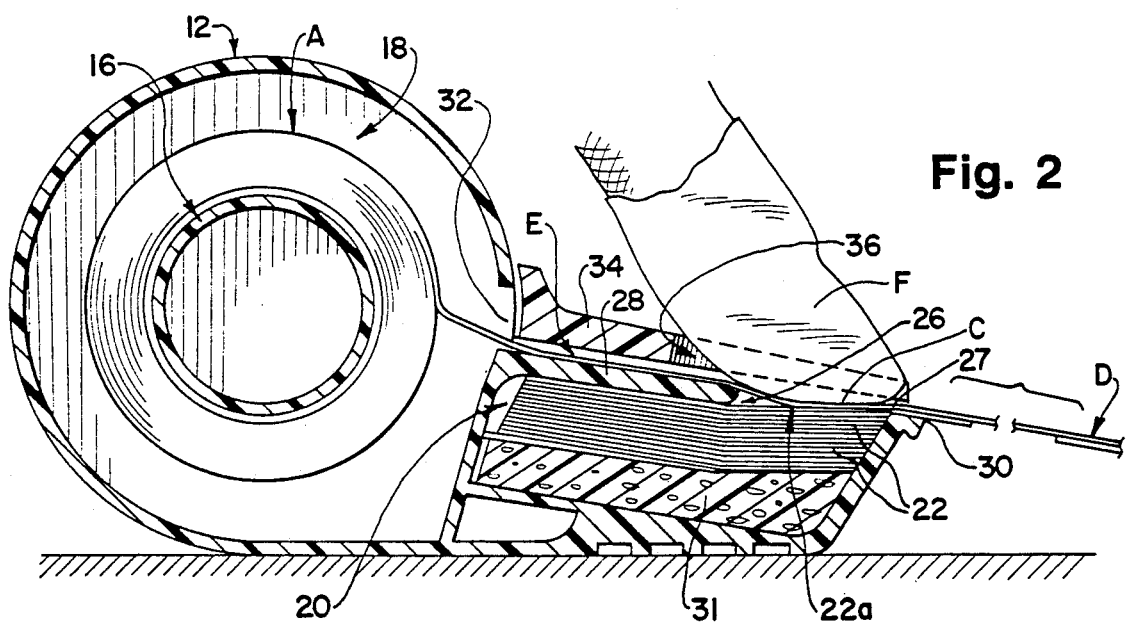
FIG. 2 is a longitudinal sectional view of the dispenser shown in FIG. 1 and further illustrating manual deflection of a tape portion to produce the covered tape joint shown in FIG. 1.

Referring to FIGS. 1 and 2, one embodiment of the tape dispenser assembly in accordance with the present invention is indicated generally by reference character 10. The dispenser 10 preferably has a molded housing 12 with a detachable sidewall 14 which is retained by conventional lip and groove joints and pin joints (not shown). The sidewall 14 is removable for installing a conventional roll of single-sided adhesive tape A for example, surgical tape, upon a spool support 16 integrally molded with the housing 12 and extending transversely within the tape compartment 18.

The dispenser assembly 10 and housing 12 also includes a second compartment 20 which holds a vertically stacked supply of individual rectangular paper tabs 22, 22. As best shown in FIG. 2, each successive uppermost tab 22a is sequentially removed from the compartment 20 through a removal aperture 26 formed in the upper compartment wall 28; the tab 22a is removed by adherence to the exposed adhesive surface B (FIG. 1) of the tape portion C aligned above the aperture 26 which is manually deflected or depressed downwardly by the finger F of the operator. The resulting tab-covered adhesive tape joint D can then be displaced to the right as shown in FIG. 2 so that the tab 22 clears the serrated tape cutting edge 30, and then the tape can be either cut or the joint D can be still further displaced until the finger F again deflects a successive tape portion C to adhere and pick up a successive paper tab 22.

Figure 3:
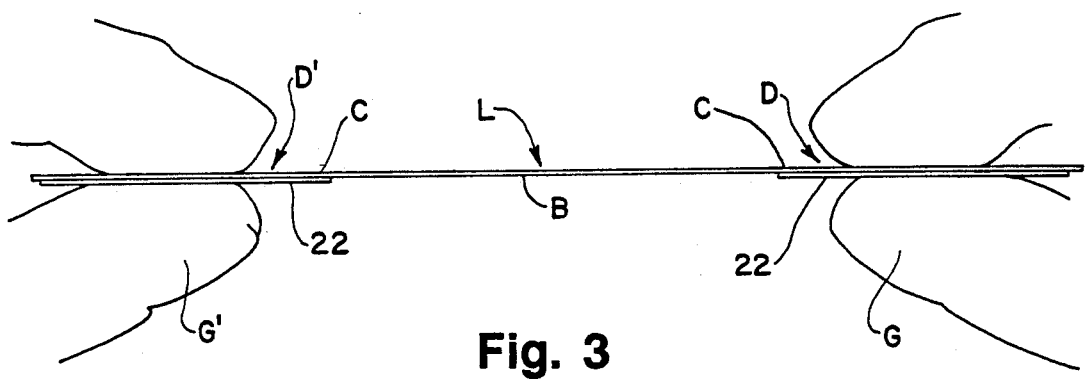
FIG. 3 is an elevational view of a length of tape having a pair of spaced, covered tape joints at the respective ends of the tape length with manual gripping of the covered adhesive at the joints.

As shown in FIG. 3, the further displacement of joint D and successive production of joint D' creates a desired length L of exposed adhesive surface B, whereupon the tape can be severed on the serrated cutting edge 30 at a point adjacently trailing the successive joint D'. The tab-covered joints D and D' enable the gloved fingers G and G' to grip the respective tabs 22, 22 of the joints D, D' while the fingers remain isolated from the adhesive surface B, so that the length L can be manipulated during subsequent procedures to apply the tape to a work object, for example a surgical dressing, without any interfering adherence of gloved fingers G, G' with the adhesive surface B. After completion of the tape application, the tabs 22 can be easily removed if desired, for example by peeling the tab from the adhesive surface B as indicated in FIG. 1.

Referring again to FIG. 2, in order to ensure that each successive uppermost tab 22a is maintained adjacently below the removal aperture 26 and readily accessible for adherence to the adhesive surface of the deflected tape portion C, the stacked arrangement of tabs 22 is seated on a resiliently compressible sponge rubber element 31 or similar biasing element which continuously elevates the stacked tabs 22 following each removal of the uppermost tab 22a. The gradient in the degree of expansion of the rubber element 31 produces a bending of tabs to feed the forward end uppermost tab 22a into the aperture. The resilient sponge rubber element 31 can be replaced by similar resiliently performing elements such as a spring loaded plate which continually feeds the uppermost tab 22a to the aperture 26.

In order to guide the tape displacement into alignment with the tab removal aperture 26, the housing 12 has a through guide aperture 32 formed adjacently above the upper compartment wall 28 which guides the exit of the tape from the compartment 18 into a guide and clearance space E formed between the upper tab compartment wall 28 and an overlying guide plate 34. As best shown in FIG. 1, the lateral edges of the guide plate 34 rest upon narrow ledges 39, 39 forming the upper surfaces of the tab compartment sidewalls 38,38 which are partially grooved at 40 to improve manual grip of the dispenser.

As best shown in FIG. 1, the guide plate 34 has a through access aperture 36 which is aligned with the removal aperture 26 to enable passage of the operator's fingertip F through the access aperture 36 for deflecting the aligned tape portion C into the adhering contact with the uppermost tab 22a as shown in FIG. 2. In the illustrated embodiment, tabs 22 have a generally elongate rectangular configuration and the tab compartment 20 has a corresponding elongate interior configuration whereas the removal aperture 26 is oriented such that its length is generally transverse and slightly wider than the width of the tape and tabs 22 as shown in FIG. 1. Accordingly, the width 25 of the aperture 26 is considerably shorter than the tabs 22 so that the tabs are removed through the aperture 26 generally from a leading aperture edge 27 in a gradual lengthwise manner as the adherence of the tab 22a also progresses lengthwise under the adhesive pull by the continued displacement of the tape and aligning portions C deflected by the fingertip F. Gradual lengthwise removal of the uppermost tab 22a maintains the generally congruent registration of the tab along the width and length of the tape as shown in the tab-covered joint D in FIG. 1, which also promotes assurance that the gloved fingers G, G' will contact only the respective tabs 22, 22 (FIG. 3) during the subsequent handling and application of the tape length L.

In light of the foregoing description of the embodied tape dispenser of the invention, it will be evident to those skilled in the design of such dispensers that various aspects may be modified without departing from the invention. As such, the scope of the invention is not limited by the particular embodiment illustrated and described herein and is defined by the appended claims and equivalents thereof.

The invention is claimed as follows:

1. A tape dispenser apparatus for dispensing adhesive tape having adhesive on a first of two opposite surfaces of the tape, comprising:
    a) a first compartment for holding a continuous length of said tape;
    b) a second compartment separated from said first compartment by a dividing wall for holding a plurality of individual cover members;
    c) guide means for guiding displacement of a portion of said tape toward said second compartment; and
    d) means for successive removal of said individual cover members and sequential adherence thereof to said adhesive surface to form covered adhesive surface portions of said tape.

2. A dispenser apparatus according to claim 1, wherein said second compartment includes a removal aperture aligned and arranged for successive removal of said individual cover members from said second compartment into registered adherence to said tape portions and said adhesive surface.

3. A dispenser apparatus according to claim 2, wherein said removal aperture has a longest dimension arranged generally transverse relative to a longest dimension of said second compartment in order that cover members defined by paper tabs dimensioned and arranged generally congruently within said second compartment are removed through said aperture in a generally lengthwise passage therethrough to promote registration with said adhesive surface.

4. A dispenser apparatus according to claim 2, wherein said guide means comprises a guide aperture formed through said first compartment for guiding removal therefrom of said portion of said tape into alignment with said removal aperture.

5. A dispenser apparatus according to claim 4, wherein said guide aperture has a longest dimension arranged generally parallel to said longest dimension of said removal aperture in order to promote registry of said cover members with said tape portions.

6. A dispenser apparatus according to claim 4, wherein said first guide aperture is elevated relative to said removal aperture in normal use in order to guide said displacement of a portion of said tape along a displacement path extending above said second compartment and plurality of cover members to enable said adhesive surface to face downwardly and said cover members to pass upwardly through said removal aperture into contact and said adherence with said adhesive tape surface facing downwardly.

7. A dispenser apparatus according to claim 1, wherein said first compartment contains a generally cylindrically wound spool of said tape.

8. A tape dispenser according to claim 1, wherein said first and second compartments are integrally formed and share a common bottom wall forming a base supporting said compartments.

9. A dispenser apparatus according to claim 2, wherein said second compartment includes upper and lower walls for containment of vertical stack of said plurality of cover members, and wherein a removal aperture opens through said upper wall such that an uppermost cover member in said vertical stack passes through said removal aperture.

10. A dispenser apparatus according to claim 9, further comprising biasing means for urging and maintaining said uppermost cover member adjacent to said removal aperture to promote passage of said uppermost cover member therethrough into adherence to said adhesive tape surface.

11. A dispenser apparatus according to claim 9, wherein said guide means comprises a guide aperture formed through said first compartment, said guide aperture having a lower periphery defined by an upper surface of said upper wall for continued guidance of said tape displacement towards said removal aperture.

12. A dispenser apparatus according to claim 9, wherein said guide means further comprises a guide element positioned narrowly spaced above said upper wall to form a clearance space therebetween through which said tape portion is passed for additional guidance towards said removal aperture.

13. A dispenser apparatus according to claim 1, further comprising severing means for severing said displaced tape portions.

14. A tape dispenser apparatus according to claim 13, wherein said severing means is arranged adjacent a terminal end of said second compartment for severing said tape following said formation of said covered adhesive surface portion.

15. A dispenser apparatus according to claim 1, further comprising biasing means for urging and maintaining said plurality of individual cover members adjacent said removal aperture to promote passage of individual cover members therethrough into adherence to said adhesive tape surface.

16. A dispenser apparatus according to claim 2, wherein said guide means further comprises a pair of narrowly spaced guide formations between which said tape portion is guided toward said removal aperture.

17. A dispenser apparatus according to claim 2, wherein said guide means further comprises a guide formation elevated relative to said second compartment to form a clearance space therebetween through which said tape is displaced into alignment above said removal aperture.

18. A dispenser apparatus according to claim 17, wherein said guide formation extends toward said removal aperture and includes an access aperture therethrough aligned with said removal aperture for passage of an operator's fingertip through said access aperture into contact with said tape portion to produce deflection of said tape portion into adherent contact with one of said cover members.

19. A dispenser apparatus according to claim 2, further comprising severing means for severing said tape wherein said severing means is arranged such that said removal aperture is located between said first compartment and said severing means in order to enable severing said tape following formation of said covered adhesive surface portion.

20. A tape dispenser apparatus for dispensing adhesive tape having adhesive on a first of two opposite surfaces of the tape, comprising:
   (a) a first supply compartment for holding a continuous length of said tape;
   (b) a second compartment holding a plurality of individual cover members; and
   (c) guide means for guiding displacement of a portion of said tape toward said second compartment for successive removal of said individual cover members and sequential adherence thereof to said adhesive surface to form covered adhesive surface portions of said tape.

21. A dispenser apparatus according to claim 20, wherein said second compartment includes a removal aperture aligned and arranged for successive removal of said individual cover members from said second compartment into registered adherence to said tape portions and said adhesive surface.

22. A dispenser apparatus according to claim 21, wherein said removal aperture has a longest dimension arranged generally transverse relative to a longest dimension of said second compartment in order that cover members defined by paper tabs dimensioned and arranged generally congruently within said second compartment are removed through said aperture in a generally lengthwise passage therethrough to promote registration with said adhesive surface.

23. A dispenser apparatus according to claim 21, wherein said guide means comprises a guide aperture formed through said first compartment for guiding removal therefrom of said portion of said tape into alignment with said removal aperture.

24. A dispenser apparatus according to claim 23, wherein said guide aperture has a longest dimension arranged generally parallel to said longest dimension of said removal aperture in order to promote registry of said cover members with said tape portions.

25. A dispenser apparatus according to claim 23, wherein said guide aperture is elevated relative to said removal aperture in normal use in order to guide said displacement of a portion of said tape along a displacement path extending above said second compartment and plurality of cover members to enable said adhesive surface to face downwardly and said cover members to pass upwardly through said removal aperture into contact and said adherence with said adhesive tape surface facing downwardly.

26. A dispenser apparatus according to claim 20, wherein said first compartment contains a generally cylindrically wound spool of said tape.

27. A tape dispenser according to claim 20, wherein said first and second compartments are integrally formed and share a common bottom wall forming a base supporting said compartments.

28. A dispenser apparatus according to claim 20, further comprising severing means for severing said displaced tape portions.

29. A dispenser apparatus according to claim 28, wherein said severing means is arranged adjacent a terminal end of said second compartment for severing said tape following said formation of said covered adhesive surface portion.

30. A dispenser apparatus according to claim 21, wherein said second compartment includes upper and lower walls for containment of a vertical stack of said plurality of cover members, and wherein a removal aperture opens through said upper wall such that an uppermost cover member in said vertical stack passes through said removal aperture.

31. A dispenser apparatus according to claim 30, further comprising biasing means for urging and maintaining said uppermost cover member adjacent to said removal aperture to promote passage of said uppermost cover member therethrough into adherence to said adhesive tape surface.

32. A dispenser apparatus according to claim 30, wherein said guide means comprises a guide aperture formed through said first compartment, said guide aperture having a lower periphery defined by an upper surface of said upper wall for continued guidance of said tape displacement towards said removal aperture.

33. A dispenser apparatus according to claim 30, wherein said guide means further comprises a guide element positioned narrowly spaced above said upper wall to form a clearance space therebetween through which said tape portion is passed for additional guidance towards said removal aperture.

34. A dispenser apparatus according to claim 21, further comprising biasing means for urging and maintaining said plurality of individual cover members adjacent said removal aperture to promote passage of individual cover members therethrough into adherence to said adhesive tape surface.

35. A dispenser apparatus according to claim 21, wherein said guide means further comprises a pair of narrowly spaced guide formations between which said tape portion is guided toward said removal aperture.

36. A dispenser apparatus according to claim 21, wherein said guide means further comprises a guide formation elevated relative to said second compartment to form a clearance space therebetween through which said tape is displaced into alignment above said removal aperture.

37. A dispenser apparatus according to claim 36, wherein said guide formation extends toward said removal aperture and includes an access aperture therethrough aligned with said removal aperture for passage of an operator's fingertip through said access aperture into contact with said tape portion to produce deflection of said tape portion into adherent contact with one of said cover members.

38. A dispenser apparatus according to claim 21, further comprising severing means for severing said tape wherein said severing means is arranged such that said removal aperture is located between said first compartment and said severing means in order to enable severing said tape following formation of said covered adhesive surface portion.

* * * * *